United States Patent [19]

Urbaschek et al.

[11] Patent Number: 4,933,322

[45] Date of Patent: * Jun. 12, 1990

[54] TREATMENT OF LEUKOCYTE AND MARROW CELL DISORDERS WITH TNF

[75] Inventors: Renate Urbaschek; Bernhard Urbaschek, both of Heidelberg; Daniela Maennel, Gaiberg, all of Fed. Rep. of Germany

[73] Assignee: BASF Aktiengesellschaft, Ludwigshafen, Fed. Rep. of Germany

[*] Notice: The portion of the term of this patent subsequent to Aug. 29, 2006 has been disclaimed.

[21] Appl. No.: 37,972

[22] Filed: Apr. 14, 1987

[30] Foreign Application Priority Data

Apr. 18, 1986 [DE] Fed. Rep. of Germany ....... 3613166

[51] Int. Cl.$^5$ ............... A61K 37/02; A61K 45/05
[52] U.S. Cl. ................... 424/85.1; 514/2; 514/12; 514/885
[58] Field of Search ............. 514/2, 12, 885; 530/351; 424/85.1

[56] References Cited

U.S. PATENT DOCUMENTS 4,275,056  6/1981  Takaku et al. ................ 424/99

FOREIGN PATENT DOCUMENTS 0250192  12/1987  European Pat. Off. .

OTHER PUBLICATIONS

Silberstein et al., (1986), Proc. Natl. Acad. Sci. U.S.A. 83:1055–1059.
Munker et al., (1986), Nature 323: 79–82.
Nature, vol. 312 (1984), pp. 724–729.
Broudy et al., cited in Chem. Abstracts, vol. 105: 189177p, 1986.
Shalaby et al., J. Immunol., vol. 135, No. 3 (Sep. 1985), pp. 2069–2073.

Primary Examiner—Jacqueline M. Stone
Attorney, Agent, or Firm—Keil & Weinkauf

[57] ABSTRACT

The use of TNF in the treatment of disorders which are accompanied by reduced leucocyte and/or marrow cell counts or functions is described.

1 Claim, No Drawings

TREATMENT OF LEUKOCYTE AND MARROW CELL DISORDERS WITH TNF

TNF (tumor necrosis factor) is a tumor-destroying substance which is intended to be used for the treatment of malignant tumors. The structure of this substance has been described in Nature 312 (1984), 724.

We have found that TNF is also useful for the treatment of disorders which are accompanied by reduced leucocyte and/or marrow cell counts or functions.

Reduced leukocyte and/or marrow counts or functions are found, in particular, after irradiation ($\alpha$-, $\beta$-, $\gamma$- or X-radiation), treatment with chemotherapeutics (for example, alkylating agents and antimetabolites) and bone marrow transplants, in aplastic anemia and agranulocytosis and after infectious diseases.

Since TNF is a polypeptide which is destroyed in the gastrointestinal tract, it can only be administered parenterally, preferably intravenously. Sterile isotonic solutions are suitable for this purpose. These can be prepared, for example, by dissolving the TNF in a blood-isotonic aqueous solution, subjecting the solution to sterile filtration and introducing it into ampoules. The pH of the solution is preferably from 5 to 8, in particular about 7.5.

The dose to be administered is from 0.1 to 5, preferably from 0.5 to 3, mg of TNF per patient per day. The duration of treatment is as a rule from 1 to 6 days.

The therapeutic efficacy of the TNF has been demonstrated, for example, as follows: C3H/HEJ and NMRI mice were treated with 0.5 $\mu$g of TNF per animal, by one intravenous administration. A dose-dependent increase in the colony stimulating activity (CSA), the neutrophilic granulocytes and hematopoietic parent cells was observed after administration of the substance, the increase being time-dependent.

PREPARATION OF AN ADMINISTRATION FORM 100 mg of TNF are dissolved in 300 ml of 20 mM sodium phosphate buffer at pH 7.5. The solution is made blood-isotonic with sodium chloride and subjected to sterile filtration over a pore filter (pore size 0.1–0.2 $\mu$m), and 5 ml portions are introduced into ampoules by a sterile procedure.

We claim:

1. The method of treating disorders which are accompanied by reduced leucocyte and/or marrow cell counts in a patient suffering therefrom, which comprises administering an effective amount of TNF.

* * * * *